(12) United States Patent
Benner et al.

(10) Patent No.: US 8,354,225 B1
(45) Date of Patent: Jan. 15, 2013

(54) AMPLIFICATION OF OLIGONUCLEOTIDES CONTAINING NON-STANDARD NUCLEOBASES

(76) Inventors: Steven Albert Benner, Gainesville, FL (US); Albert Michael Sismour, Gainesville, FL (US)

( * ) Notice: Subject to any disclaimer, the term of this patent is extended or adjusted under 35 U.S.C. 154(b) by 718 days.

(21) Appl. No.: 11/371,497

(22) Filed: Mar. 9, 2006

Related U.S. Application Data

(63) Continuation-in-part of application No. 11/212,225, filed on Aug. 27, 2005, now abandoned.

(60) Provisional application No. 60/605,062, filed on Aug. 28, 2004.

(51) Int. Cl.
| | |
|---|---|
| *C12Q 1/68* | (2006.01) |
| *C12P 19/34* | (2006.01) |
| *A01N 43/04* | (2006.01) |
| *A61K 31/70* | (2006.01) |
| *C07H 21/02* | (2006.01) |
| *C07H 21/04* | (2006.01) |

(52) U.S. Cl. ...... 435/6.1; 435/91.2; 536/23.1; 536/29.2; 514/23

(58) Field of Classification Search .................. None
See application file for complete search history.

(56) References Cited

OTHER PUBLICATIONS

Sismour et al. Nucleic Acids Research vol. 32:729-735. 2004.*
Horlacher, J., Hottiger, M., Podust, V.N., Huebscher, U., Benner, S.A. (1995) Recognition by viral and cellular DNA polymerses of nucleosides bearing bases with non-standard hydrogen bonding patterns. Proc. Natl. Acad. Sci. USA 92, 6329-6333.
Sismour, A. M., Lutz, S., Park, J.-H., Lutz, M. J., Boyer, P. L., Hughes, S. H., Benner, S. A. (2004) PCR amplification of DNA containing non-standard base pairs by variants of reverse transcriptase from human immunodeficiency virus-1. Nucleic Acids Res. 32, 2, 728-735.
Sismour, A. M., Benner, S. A. (2005) The use of thymidine analogs to improve the replication of an extra DNA base Pair: A synthetic biological system. Nucleic Acids Res. 33, 17, 5640-5646.
Yang, Z., Nutter, D., Sheng, P., Sismour, A. M., Benner, S. A. (2006) Artificially expanded genetic information system: A new base pair with an alternative hydrogen bonding pattern. Nucleic Acids Res. 34, 21, 6095-6101.
Yang, A., Sismour, A. M., Sheng, P., Puskar, N. L., Benner, S. A. (2007) Enzymatic incorporation of a third nucleobase pair. Nucleic Acids Res. 35, 13, 4238-4249.
Kimoto, M., Kawai, R., Mitsui, T., Yokoyama, S., Hirao, I. (2009) An unnatural base pair system for efficient PCR amplification and functionalization of DNA molecules. Nucleic Acids Res., 37, e14.
Chen, F., Gaucher, E. A., Leal, N. A., Nutter, D., Havemann, S. A., Govindarajan, S., Ortlund, E. A., Benner, S. A. (2010) Reconstructed evolutionary adaptive paths (REAP) give polymerases accepting reversible terminators for sequencing and SNP detection. Proc. Natl. Acad. Sci. USA 107, 5,1948-1953.

\* cited by examiner

*Primary Examiner* — Teresa E Strzelecka

(57) ABSTRACT

This invention relates to nucleoside, nucleotide, and oligonucleotide analogs that incorporate non-standard nucleobase analogs, defined to be those that present a pattern of hydrogen bonds to a paired nucleobase analog in a complementary strand that is different from the pattern presented by adenine, guanine, cytosine, and thymine. Most specifically, this invention discloses and claims processes for amplifying nucleic acid analogs containing non-standard nucleobases using polymerase chain reactions, and enzymes that perform this amplification.

9 Claims, 7 Drawing Sheets

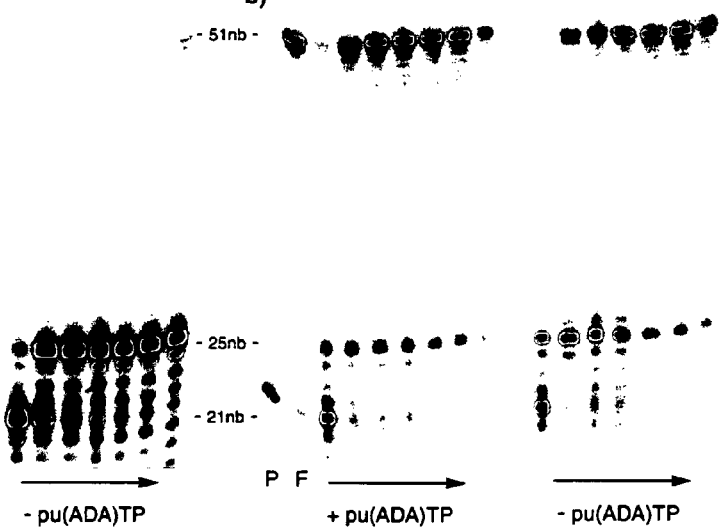

Figure 6
51-
25-
21-
P T DV F

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial sequence
<220> FEATURE:
<223> OTHER INFORMATION: synthetic sequence

<400> SEQUENCE: 1
gcgaattaac cctcactaaa g                                              21

<210> SEQ ID NO 2
<211> LENGTH: 21
<212> TYPE: DNA
<213> ORGANISM: Artificial sequence
<220> FEATURE:
<223> OTHER INFORMATION: synthetic sequence

<400> SEQUENCE: 2
gcgtaatacg actcactata g                                              21

<210> SEQ ID NO 3
<211> LENGTH: 25
<212> TYPE: DNA
<213> ORGANISM: Artificial sequence
<220> FEATURE:
<223> OTHER INFORMATION: synthetic sequence

<400> SEQUENCE: 3
gcgaattaac cctcactaaa gaacg                                          25

<210> SEQ ID NO 4
<211> LENGTH: 25
<212> TYPE: DNA
<213> ORGANISM: Artificial sequence
<220> FEATURE:
<223> OTHER INFORMATION: synthetic sequence

<400> SEQUENCE: 4
gcgtaatacg actcactata gacga                                          25

<210> SEQ ID NO 5
<211> LENGTH: 27
<212> TYPE: DNA
<213> ORGANISM: Artificial sequence
<220> FEATURE:
<221> NAME/KEY: misc_feature
<222> LOCATION: (6)..(6)
<223> OTHER INFORMATION: a nonstandard nucleotide of the instant
      invention
<220> FEATURE:
<223> OTHER INFORMATION: Synthetic

<400> SEQUENCE: 5
atgcangcgt aatacgactc actatag                                        27
```

```
<210> SEQ ID NO 6
<211> LENGTH: 21
<212> TYPE: DNA
<213> ORGANISM: Artificial sequence
<220> FEATURE:
<223> OTHER INFORMATION: synthetic sequence

<400> SEQUENCE: 6
cgcattatgc tgagtgatat c                                            21

<210> SEQ ID NO 7
<211> LENGTH: 18
<212> TYPE: DNA
<213> ORGANISM: Artificial sequence
<220> FEATURE:
<223> OTHER INFORMATION: synthetic sequence

<400> SEQUENCE: 7
caggaaacag ctatgacg                                                18

<210> SEQ ID NO 8
<211> LENGTH: 51
<212> TYPE: DNA
<213> ORGANISM: Artificial sequence
<220> FEATURE:
<223> OTHER INFORMATION: synthetic sequence

<400> SEQUENCE: 8
gcgtaatacg actcactata gacgttcgtt ctttagtgag ggttaattcg c            51

<210> SEQ ID NO 9
<211> LENGTH: 51
<212> TYPE: DNA
<213> ORGANISM: Artificial sequence
<220> FEATURE:
<223> OTHER INFORMATION: synthetic sequence

<400> SEQUENCE: 9
gcgaattaac cctcactaaa gtacgttcgt ctatagtgag tcgtattacg c            51

<210> SEQ ID NO 10
<211> LENGTH: 51
<212> TYPE: DNA
<213> ORGANISM: Artificial sequence
<220> FEATURE:
<221> NAME/KEY: misc_feature
<222> LOCATION: (26)..(26)
<223> OTHER INFORMATION: a nonstandard nucleotide of the instant
      invention
<220> FEATURE:
<223> OTHER INFORMATION: Synthetic

<400> SEQUENCE: 10
gcgtaatacg actcactata gacgtncgtt ctttagtgag ggttaattcg c            51

<210> SEQ ID NO 11
<211> LENGTH: 51
<212> TYPE: DNA
<213> ORGANISM: Artificial sequence
<220> FEATURE:
<221> NAME/KEY: misc_feature
<222> LOCATION: (26)..(26)
<223> OTHER INFORMATION: a nonstandard nucleotide of the instant
      invention
<220> FEATURE:
<223> OTHER INFORMATION: Synthetic

<400> SEQUENCE: 11
```

```
gcgaattaac cctcactaaa gtacgntcgt ctatagtgag tcgtattacg c        51
```

<210> SEQ ID NO 12
<211> LENGTH: 33
<212> TYPE: DNA
<213> ORGANISM: Artificial sequence
<220> FEATURE:
<221> NAME/KEY: misc_feature
<222> LOCATION: (23)..(23)
<223> OTHER INFORMATION: a nonstandard nucleotide of the instant
      invention
<220> FEATURE:
<223> OTHER INFORMATION: Synthetic

<400> SEQUENCE: 12

```
cgtcatagct gtttcctggt ccncgcattg ctg                            33
```

AMPLIFICATION OF OLIGONUCLEOTIDES CONTAINING NON-STANDARD NUCLEOBASES

CROSS REFERENCE TO RELATED APPLICATIONS

This application is a continuation in part of Ser. No. 11/212,225, filed 27 Aug. 2005, now abandoned, which claimed the priority of U.S. Provisional Application 60/605,062 filed 28 Aug. 2004

STATEMENT OF RIGHTS TO INVENTIONS MADE UNDER FEDERALLY SPONSORED RESEARCH

This invention was made with government support awarded by the National Institutes of Health GM003581. The government has certain rights in the invention.

FIELD

This invention relates to the field of nucleic acid chemistry, more specifically to the field of nucleic acid analogs, and most specifically to oligonucleotide analogs that incorporate non-standard nucleobases, those that present to a complementary strand in a Watson-Crick pairing geometry a pattern of hydrogen bonds that is different from the pattern presented by adenine, guanine, cytosine, and thymine. Most specifically, this invention discloses and claims processes for amplifying nucleic acid analogs containing non-standard nucleobases.

BACKGROUND

Artificial genetic systems have been the targets of organic chemists for more than a decade.[1,2,3,4] They have recently attracted attention in the scientific literature[5,6,7] and the science press.[8,9] One class of these retains the two rules of complementarity that characterize standard Watson-Crick base pairing: (i) size complementarity, whereby a large purine pairs with a small pyrimidine, and (ii) hydrogen bonding complementarity, whereby hydrogen bond donors complement hydrogen bond acceptors.[10]

With three hydrogen bonds joining the paired nucleobases, twelve nucleobases and six mutually exclusive hydrogen bonding patterns are possible (FIG. 1). These were preared some time ago by Benner as part of an Artificially Expanded Genetic Information System (AEGIS). Diagnostics products based on AEGIS have been approved from the Food and Drug Administration for clinical use to monitor viral load in patients living with HIV and hepatitis C.[11]

As is widely recognized by those skilled in the art, it would be useful to be able to amplify the oligonucleotides containing non-standard components in a process analogous to the well known polymerase chain reaction. This might even allow an artificial genetic system to be incorporated into a living cell.[12] This would in particular be useful for doing in vitro selection, Selex, and in vitro evolution of an expanded genetic information system for the purpose of creating new catalysts, ligands, and receptors.

Some time ago, Benner patented a process for doing this [U.S. Pat. No. 5,965,364]. This process has never, however, been executed. This is because the specification of U.S. Pat. No. 5,965,364 did not disclose a polymerase that incorporates a non-standard base pair into a duplex with sufficient efficiency and fidelity to support such a process. This was illustrated by Johnson et al.[13], who attempted to incorporate iso-cytosine and isoguanine into a PCR-type process. As their publication shows, the non-standard component is not retained, to an extent of at least 90% over 5 cycles, in the product. This can be taken as a crude metric for the utility of a PCR process that incorporates a non-standard nucleobase.

The difficulty in incorporating AEGIS components into a PCR process may be due to difficulties in the efficiency by which polymerases interact with unnatural nucleoside triphosphates. Many enzymes work well with AEGIS components, including kinases, ligases, and even ribosomes.[14] Polymerases, in contrast, accept many non-standard components of DNA only inefficiently, judging by rate, processivity, fidelity, or some combination of these.[15] These inefficiencies need not prevent the utility of polymerase-based incorporation of AEGIS components in single pass experiments, and may not be apparent with standing start experiments, where the non-standard triphosphate is the first nucleotide to be added to a primer, or a running start experiment, where the polymerase adds standard nucleotides before it is challenged to incorporate a non-standard nucleotide.

Without expressing an opinion about why Johnson et al. failed to generate a useful PCR process, it would nevertheless be useful to be able to amplify via the polymerase chain reaction such oligonucleotide analogs (herein referred to as "oligonucleotides", despite their not being standard, natural oligonucleotides), so that a small number of starting oligonucleotides can generate multiple product oligonucleotides, through the copying of oligonucleotides containing AEGIS components, and then copying the copies.

While it is recognized that such processes invariably introduce some mutations, and that some of the daughter oligonucleotides will not have the exact identical sequence as the original oligonucleotide (and indeed, this evolution is useful in some contexts), PCR amplification of these oligonucleotides would be most useful if the level of mutation is lower rather than higher, preferably less than a 5% loss of the non-standard nucleobase per cycle, and more preferably less than a 2% loss of the non-standard nucleobase per cycle, and most preferably retaining 90% of the AEGIS component after 5 cycles.

The object of the instant invention is to provide a process that does PCR amplification of AEGIS-containing oligonucleotides with two specific AEGIS components, one presenting the donor-acceptor-donor hydrogen bonding pattern on a pyrimidine skeleton, hence described as the pyDAD system, herein implemented on the diaminopyrimidine heterocycle, the other presenting the hydrogen bond acceptor-donor-acceptor hydrogen bonding pattern on a purine skeleton, hence described as the puADA system, herein implemented on the xanthosine heterocycle.

Also obvious to one of ordinary skill in the art, to be useful, the PCR process exploiting AEGIS components must be associated with a sequencing tool that allows the practitioner of the art to assess the extent to which the AEGIS component has been retained in the PCR products. It is the object of the instant invention to provide a provide a process for doing so.

BRIEF DESCRIPTION OF THE DRAWINGS

FIG. 2. Primer extension experiments with two HIV-RT variants, Y188L (gel a) and M184V (gel b). For each, the variant was incubated, for times ranging from 1 min to 1440 min (right to left, in direction of arrow, with template T2-κ, radiolabeled primer P2-RS, dATP, dGTP, dCTP, and dTTP, and either with the complementary d(puADA)TP (left panel of each gel) or without d(puADA)TP (right panel of each gel).

Time points are at 1, 30, 60, 120, 240, 480, and 1440 min. P is the unextended primer, 21 nts in length. F is full length product, following addition of 30 nucleotides to the primer.

Figure 1:
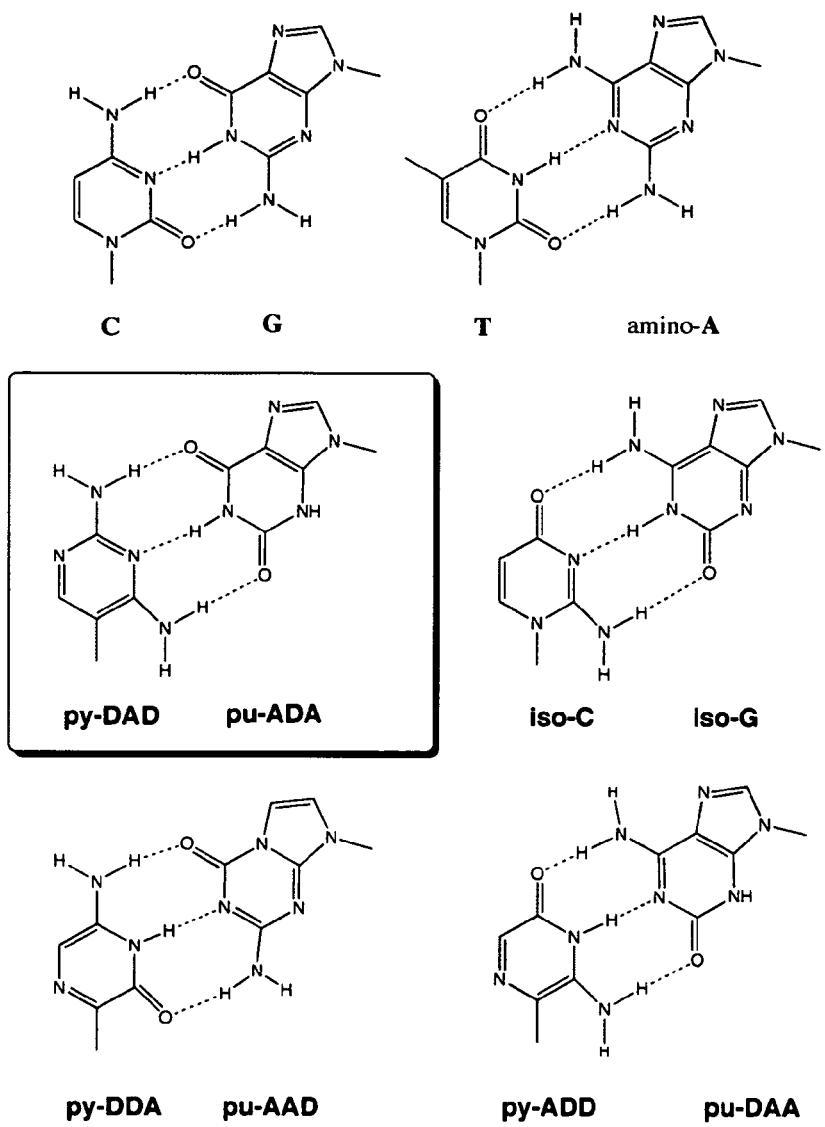
FIG. 1. An artificially expanded genetic alphabet.
Figure 3:
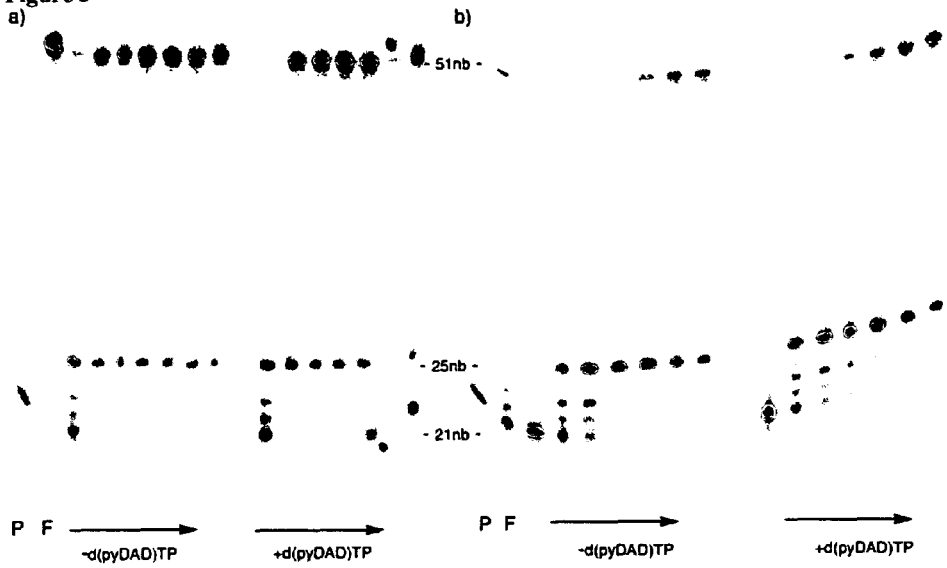

FIG. 3. Primer extension experiments with two candidate HIV-RT variants, Y181I (gel a) and Y188L (gel b). For each, the variant was incubated, for times ranging from 1 min to 480 min (right to left, in direction of arrow), with template T1-X, radiolabeled primer P1-RS, dATP, dGTP, dCTP, and dTTP, and either with the complementary d(pyDAD)TP (left panel of each gel) or without d(pyDAD)TP (right panel of each gel). The data suggest that HIV-RT variant Y188L both produced a slightly higher ratio of full-length product in the presence of d(pyDAD)TP to full length product in the absence of d(py-DAD)TP, while variant Y181I produced a lower ratio. This made Y188L the prime candidate for further examination.

Figure 4:
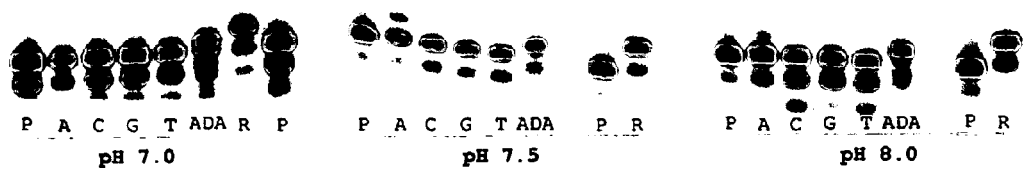

FIG. 4. Single nucleotide primer extension experiments as a function of pH with Y188L. Variant Y188L was incubated for 30 min at the pH indicated, with template T2-pyDAD, radiolabeled primer P2-SS and one of the four standard deoxynucleoside triphosphates or d(puADA)TP. Lane P (primer alone); Lane A, with dATP; Lane C, with dCTP; Lane G, with dGTP; Lane T, with TTP; Lane ADA, with d(puADA)TP, Lane R, positive control with substitution of T2 for T2-py-DAD, thus having dA instead of the non-standard nucleotide. Noticeable in all experiments is the primer band (labelled P) and a degradation band (below the primer band); the degradation of the primer was due to a DNAse activity of the reverse transcriptase itself, an activity that was removed by the mutation E478Q (see text). Little incorporation was observed at pH<6.5; the optimal pH was 7.0-7.5. It should be noted that oligonucleotides containing a puADA residue migrate slightly faster due to the negative charge on the heterocycle.

Figure 5:
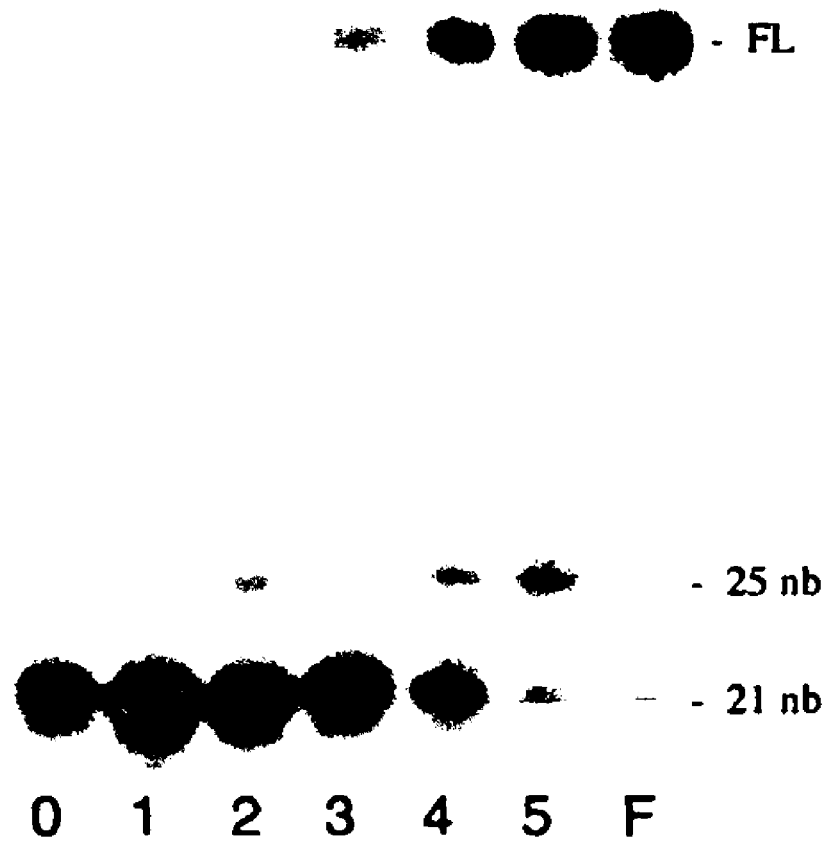

FIG. 5. PCR amplification (from left to right, 0 to 5 rounds, each 24 hours) of template T2-py(DAD) using primers P2-C6 and P2-Rev in the presence of dNTPs, d(puADA)TP, and d(pyDAD)TP (200 µM each), showing the appearance of full length product, seen in the positive control labeled F, using the double variant HIV-RT Y188L E478Q. Note the absence of degradation of primer due to the knockout of the nuclease activity via the E478Q mutation. Reverse transcriptase was added at each cycle.

FIG. 6. Use of Taq and DeepVent (DV) exo+ polymerases as sequencing tools. Both polymerases were incubated with template T3, primer P3, and dNTPs. P=primer alone, 19 nts in length. Both polymerases abort elongation upon encountering dX in the template, but efficiently generate (as expected) full length products when challenged with templates containing only A, T, G, and C. Deep Vent exo appears to be degrading the primer, and perhaps the product as well.

Figure 7:
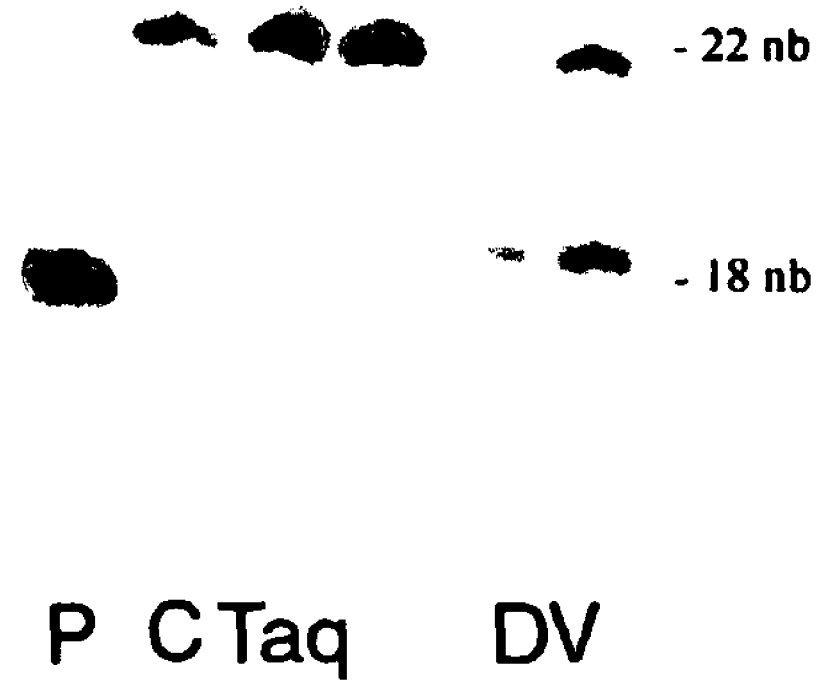

FIG. 7. Proof that the PCR product (from round 5) contained dX nucleotide. Primer extension experiment with primer P2-Rev and the product of round 5 of the PCR experiment, with Taq and DeepVent polymerases. Pausing at position 25 demonstrates the presence of neither A, T, G, or C at this position. Generation of <5% full length product establishes <5% misincorporation of the standard nucleotides after 5 rounds of PCR amplification.

DESCRIPTION OF THE INVENTION

To identify polymerases that enabled the PCR amplification of oligonucleotides containing the pair between 2,4-diaminopyrimidine (pyDAD) and xanthine (puADA), variants of HIV reverse transcriptase (RT) were examined for their ability to synthesize duplex DNA incorporating this non-standard base pair. This base pair fits the Watson-Crick geometry, but is joined by a pattern of hydrogen bond donor and acceptor groups different from those joining the GC and AT pairs. A variant of HIV-RT where Tyr 188 is replaced by Leu, which emerged from experiments where HIV was challenged to grow in the presence of drugs targeted against the reverse transcriptase, such as L-697639, TIBO, and nevirapine, was used as a starting point. These drugs bind at a site near, but not in, the active site. This variant accepts the pyDAD-puADA base pair significantly better than wild type HIV-RT, with the efficiency and fidelity that met the specifications.

This is an exemplification of a novel, inventive process, in clinico selection, for obtaining variants of enzymes that are certain to retain one of their useful properties, activity with their natural substrates, as they continue to support life in the natural system, but may have novel additional useful properties, in this case, a new interaction with an unnatural substrate, in this case, the 2,4-diaminopyrimidine (pyDAD) and xanthine (puADA) nucleosides in templates and presented as triphosphates. More generally, this exemplifies a process for obtaining variants of a preselected enzyme that have one or more new and useful properties, while retaining useful native catalytic activities found in the native enzyme, and thereby creating a variant that has a combination of useful properties, some of which are new and others of which are not, but where both are required for the variant to be useful. This process comprises presenting to individuals in a population (where the population can be human, but can also be animal or microbial) one or more drugs and/or other biologically active composition, whose mechanism of action is based on their binding to the target enzyme, recovering from the population variants of the enzyme that have emerged in response to the presentation of said drug and/or compositions, and screening the variants for the new and useful property.

To further improve the utility of the Y188L variant, a second mutation, E478Q, was introduced into the Y188L variant, by design. Here, the design was intended to remove the residual nuclease activity that was hypothesized to be intrinsic in the nuclease site of RT. The alternative hypothesis is that nuclease activity observed was due to a contaminant.

While not wishing to be bound by theory, our presently preferred polymerase for PCR amplification of this non-standard base pair is the doubly mutated RT. Experimental data, discussed below, showed that this polymerase incorporated the non-standard pair with sufficient fidelity that the variant could be used to amplify oligonucleotides containing pyDAD and puADA through several rounds of a polymerase chain reaction (PCR) without losing the non-standard base pair, and certainly not to the extent that less than 90% was retained after 5 rounds. Indeed, this polymerase met our most preferred specification, retaining more than 95% after 5 rounds.

This is the first time where DNA containing non-standard base pairs with alternative hydrogen bonding patterns has been amplified by a full PCR reaction.

To demonstrate incorporation of the pyDAD-puADA pair repeatedly in the PCR cycles, and to quantitated the extent of its retention throughout these cycles, the pause-based sequencing strategy was invented. An enzymatic process for 'paused-based' sequencing of pyDAD and/or puADA nucleotide(s) in DNA using a polymerase that cannot incorporate a natural deoxynucleoside triphosphate opposite the pyDAD and/or puADA nucleotide(s).

EXAMPLES

Synthesis of Non-Standard Nucleosides 2,4-Diamino-5-(β-D-ribofuranosyl)pyrimidine (pyDAD) was synthesized via a route adapted from Chu et al.,[16] converted to the 2'-deoxygenated nucleoside analog via the route described previously.[17] 5'-Dimethoxytrityl-2'-deoxyxanthosine with both heterocyclic ring oxygens protected as p-nitrophenylethyl ethers was prepared by a procedure adapted from Van Aerschot et al.[18,19] Both were then converted to the phosphoramidite suitable for automated DNA synthesis.[20]

To prepare 2'-deoxyxanthosine-5'-triphosphate d(puADA)TP, 2'-deoxyguanosine triphosphate (sodium-salt, 10 mg, 16.7 mmol) was dissolved in water (220 µL) containing sodium nitrite (10 mg, 80 mmol). A mixture of HCl (8.7 µL, 4 L, 2 M) and acetic acid (glacial, 25 µL) was added and the sample incubated at RT for 3 h. The reaction was quenched with Tris base (400 µL, 1 M). The raw material can be stored at −20° C. before being purified by RP-HPLC (Nova Pak C-18 Radial Pak cartridge (Waters), 25×100 mm, TEAA (100 mM, pH 7), linear gradient to 10% acetonitrile over 25 minutes). The combined product fractions were lyophilized and the residue was dissolved in Tris-HCl (2 mL, 10 mM, pH 7.0). The yield of 16 was determined by UV absorbance (4.2 mg, 42%, 247/277 nm, $\epsilon$=10,000/9100 $M^{-1}$ $cm^{-1}$). The purity of the material was >97% as determined by analytical RP-HPLC and anion-exchange HPLC [Macrosphere 300A WAX 7U (Alltech, Deerfield Ill.)] 4.6 mm×250 mm; solvent A=water; solvent B=TEA-bicarbonate (0.8 M, pH 7.2); curved gradient (#7) from 1% to 50% B in 15 min).

The triphosphate d(pyDAD)TP was synthesized via published procedures from the nucleoside.[21]

Oligonucleotide Synthesis: Primers and Templates.

The oligonucleotide sequences used in this work are listed Table 1. Oligonucleotides bearing non-standard bases were prepared by "trityl off" solid-phase synthesis using an Applied Biosystems automated DNA synthesizer from the β-cyanoethyl protected phosphoramidites. They were purified by PAGE (12-20%). Those oligonucleotides containing only standard nucleotides were obtained commercially from Integrated DNA Technologies (Coralville, Iowa).

Enzyme Expression and Purification

The HIV reverse transcriptases were expressed as p66/p51 heterodimers using a plasmid that coexpresses the p66 coding region of the HIV-1 RT variant, with a hexahistidine tag on the C-terminus, and HIV-1 protease. The expression is induced by the addition of IPTG, and a polycistronic messenger containing both the RT and protease coding region is produced. In the E. coli, the protease cleaves the p66 homodimer to yield the p66/p51 heterodimer with a hexahistidine tag only on the p66 subunit.[29] The enzymes were isolated by the procedure of Boyer et al.[22]

Determining the Catalytic Activity of the Enzymes

Enzyme activity was determined by incorporation of [$^3$H]-TTP into a poly(rA)-oligo(dT) template.[23,24,25,26] All reactions were carried out at 37° C. in a water bath. An aliquot of the reverse transcriptase (1-2 µL) was incubated in HIV-RT buffer (Tris-HCl 50 mM, pH 7.2, $MgCl_2$, 5 mM, KCl 100 mM, DTT, 1 mM, EDTA 0.5 mM) in the presence of 5 µg poly(rA)-oligo(dT)$_{12-18}$ (Pharmacia) and [$^3$H]-TTP (25 µM, 6000 cpm/pmol, Amersham; concentration adjusted with 1 mM TTP). Four aliquots (20 µL) were taken over a 12 min period and quenched with EDTA (10 µL, 0.5 M, pH 8). The quenched reaction mixture (20 µL) was applied to 2.5-cm circles of Whatman DE-81 filter paper. The air-dried filter papers were washed three times with $Na_2HPO_4$ solution (0.15 M), twice with EtOH, and finally once with $Et_2O$. The dry filters were counted by liquid scintillation counting in ScintiSafe (30%, 5 mL, Fisher). All experiments were repeated three times and the resulting data averaged. The activity was calculated from the slope of a time vs. cpm plot and was expressed as units per mL (U/mL). One unit of enzyme was defined as the amount of polymerase that converts 1 nmol TTP into filter-bound material in 10 min at 37° C.

Enzyme variants had the following specific activities (tested on poly(rA)/oligo(dT)): HIV-1 RT heterodimer: 8700 units/mg; Variant L74V: 9750 units/mg; Variant K103N: 11300 units/mg; Variant Y181I: 7500 units/mg; Variant M184V: 10600 units/mg; Variant Y188L: 5100 units/mg; Variant AZT-21 (M41L, D67N, K70R, T215Y, K219Q): 4150 units/mg; Variant Y188L, E478Q: 5100 units/mg.

Running Start Experiments.

In a typical primer extension experiment, 5'-$^{32}$P-labeled primer (P1-RS) and template T1, or P2-RS and template T2 (656 nM of the primers, 920 nM of the templates) in HIV RT buffer were mixed with dATP, dGTP, dCTP, and TTP (final concentration 130 µM each) in a total volume of 160 µL. In experiments with nonstandard nucleotides, the concentrations for d(pyDAD)TP and d(puADA)TP were also 130 µM. After heating the sample to 95° C. for 1 min, the primer/template complex was annealed by cooling to room temperature over 1 h. Primer extension was started by addition of the reverse transcriptase (16 µL). The mixture was then incubated at 37° C. Aliquots (25 µL), taken at various times during the reaction, were quenched by addition of a premixed solution of sodium acetate (2.5 µL, 3 M, pH 5.2), EDTA (1 µL, 0.5 M, pH 8), and ethanol (50 µL). After being stored at −20° C. for 20 min, the samples were centrifuged (14,000 rpm, 4° C., 20 min) and the pellets dried in the vacuum concentrator. The residues were redissolved in PAGE loading buffer and the samples separated on a 10% PAGE gel (7 M urea). The gel was analyzed using the MolecularImager®.

To improve reproducibility in cases where multiple reactions were run in parallel, a master mixture of primer/template and the dNTPs was prepared by scaling up the listed procedure. Master mixtures were not stored for more than 24 hours at −20° C.

Standing Start Experiments.

Primer P1-SS or P2-SS (15 pmol, 5'-$^{32}$P-labeled) and the appropriate template (T1 or T2, 21 pmol) were incubated with HIV RT at a range of pHs (8 µL, 3×) and the volume adjusted with water to 2 µL with water. The DNA was denatured (95° C., 1 min) and cooled to room temperature (1 h). After addition of the appropriate dNTP (1.67 µL, 130 µM final concentration of each) and an aliquot of reverse transcriptase (0.2 U). The mixture was incubated for up to 30 min at 37° C. The reaction was quenched by addition of a premixed solution of sodium acetate (2.5 µL, 3 M, pH 5.2), EDTA (1 µL, 0.5 M, pH 8), and EtOH (50 µL), the DNA was recovered by centrifugation, and the pellet was dried in the vacuum concentrator. The DNA was dissolved in PAGE loading buffer (Bromphenol blue/xylene cyanol mix 0.1 g, water, 1 mL, and formamide, 4 mL) and analyzed using a 10% PAGE gel (7 M urea). The gel was analyzed with the MolecularImager®.

PCR Amplification.

To facilitate strand separation, one of the PCR primers (P2-C6) was designed to contain a tetranucleotide appended to the 5'-position via two C6 polyethyleneglycol units. This made the product derived from the primer move slower in a gel electrophoresis experiment than the product derived from the reverse primer.

Template T2-pyDAD (50 pmol) was mixed with 5'-radiolabeled primer P2-C6 (750 pmol), primer P1-RS (750 pmol), dATP, dTTP, dCTP, dGTP, d(puADA)TP, d(pyDAD)TP (final conc. 200 µM each), HIV RT buffer (333 µL, 3×), and the reaction volume adjusted to 1 mL with water. The mixture was heated to 95° C. (10 ml) and allowed to cool to ambient temperature (1 h). HIV RT (Y188L, E478Q) (10 U) was added to the reaction mixture, which was then incubated at 37° C. for 24 hours. An aliquot (5 µL) was removed and quenched with 20 mM EDTA in formamide (5 µL). The remaining reaction mixture was heated again to 95° C. for 10 minutes and again cooled to ambient temperature over 1 hour. Another aliquot of RT was then added. This cycle was repeated 4 times. The products from each round of PCR amplification were resolved using a 12% PAGE gel (7 M urea). The gel was analyzed using the MolecularImager software. A positive control experiment was run under the same conditions while substituting T-2 for T2-pyDAD.
PCR Product Isolation.

The PCR reaction was quenched with EDTA (final conc. 10 mM) and the DNA isolated via ethanol (2.5 mL) precipitation and subsequently washed with 70% ethanol in water. The dry pellet was dissolved in PAGE loading buffer and analyzed by electrophoresis on a 20% PAGE gel (7 M urea). The product generated from full extension of primer P2-C6 was longer, and therefore moved slower, than the product generated from the full extension of P2-Rev. The product from full extension of P2-C6 was cut from the gel and extracted by incubating in a crush and soak buffer (0.1% SDS, 0.5 M $NH_4OAc$, 10 mM $Mg(OAc)_2$) at 37° C. overnight. The solution was filtered through a Millipore filter (0.45 pore size) and the DNA recovered by ethanol precipitation. The DNA pellet (T1-X-PCR) was dissolved in water to a final concentration of 10 µM.
Paused-Extension Sequencing.

T1-puADA-PCR (2 pmol, presumably generated by the PCR reaction) was mixed with radiolabeled P2-Rev (1 pmol), Thermopol buffer (final conc. 20 mM Tris-HCl, pH 8.8, 10 mM KCl, 10 mM $(NH_4)_2SO_4$, 2 mM $MgSO_4$, 0.1% Triton X-100), dATP, dCTP, dTTP, dGTP (final conc. 10 µM each), and the reaction volume was adjusted to 14 µL with water. Heating (95° C., 10 min) and cooling to ambient temperature (1 hour) the respective polymerase (reaction I with Taq, reaction 2 with Vent exo+) was added (1 µL, □U/µL) and the mixture was incubated at 72° C. for 15 seconds. A positive control was run under the same conditions by substituting T1 for T1-X-PCR. The reactions were quenched by addition of PAGE loading buffer containing 20 mM EDTA (15 µL). The samples were subjected to electrophoresis on a 20% PAGE gel and the gel analyzed using the MolecularImager software.
Paused-Extension Screen.

Radiolabeled primer P3 (1 pmol) was mixed with template T3 (2 pmol), Thermopol buffer (1.5 µL, 10×), dATP, dCTP, dTTP, dGTP (final conc. 10 µM each), and water to a final volume of 14 µL. The mixture was heated to 95° C. for 10 min. and allowed to cool to ambient for 1 hour. The respective polymerase (Taq, Vent, Deep Vent, Vent exo−, or Deep Vent exo−) was added (1 µL, 2 U/µL) and the reaction incubated at 72° C. for 15 seconds. The reaction was quenched with 20 mM EDTA in PAGE loading buffer (15 µL) and subsequently analyzed by electrophoresis on a 20% PAGE gel. The gel was analyzed using the MolecularImager software.
PCR Primer extension experiments were performed for the four variant forms of HIV-RT (Y181I, Y188L, M184V, and AZT-21). Each was challenged to incorporate a single d(puADA) nucleotide opposite a d(pyDAD) at position 26 in the template (T2-K), five nucleobases upstream of the 3'-end of the primer. Experiments were done in parallel, one containing only standard nucleoside triphosphates (the "minus" control), the other containing the standard dNTPs plus d(puADA)TP. The progress of the primer extension reaction was followed by PAGE on samples removed at intervals.

Results of these experiments suggest that HIV-RT variants Y188L (FIG. 2) and Y181I (data not shown) both produced more full-length product in the presence of d(puADA)TP than in its absence, while variants AZT-21 (data not shown) and M184V (FIG. 2) did not. This made variants Y188L and Y181I candidates for further polymerase development.

Primer extension experiments testing the incorporation of d(pyDAD)TP opposite d(puADA) in the template were then performed with these candidates. Variants Y188L and Y181I were incubated (1 to 480 min) with the standard triphosphates with and without the complementary d(pyDAD)TP. The results (FIG. 3) suggest that Y188L produced a slightly higher ratio of full-length product in the presence of d(pyDAD)TP to full length product in the absence of d(pyDAD)TP, while variant Y18 µl produced a lower ratio. This made Y188L the prime candidate for further examination.

Both pu(ADA) and py(DAD) display acid-base chemistry. The heterocycle of pu(ADA) is an acid with a $pK_a$ of ca. 5.7.[27] In contrast, py(DAD) is protonated, and the conjugate acid was measured to have a $pK_a \approx 6.7$.[28] A series of single nucleotide primer extension experiments were therefore performed with Y188L to identify the nucleotides most likely to compete with the nonstandard nucleotides during primer extension, and to assess the impact of pH on incorporation.

To determine the optimal pH for d(puADA)TP incorporation, Y188L was incubated at pH 5.5 to 7.5. The results (FIG. 4) showed little incorporation at pH<6.5. The optimal pH was between 7.0 and 7.5. While we do not know the exact $pK_a$ of either py(DAD) or pu(ADA) heterocycles when incorporated into an oligonucleotide, they are likely to be higher than 6.7 and 5.7. Therefore, it is possible that at the optimal pH for this reaction, the pu(ADA)-py(DAD) pair is an anion-cation pair.

Noticeable in all gels is a band below the primer band. This was not due to a failure in the synthesis of the primer. Rather, the band appeared to arise through degradation caused by a DNAse activity present in the reaction mixture. The two possible origins of this activity are contamination, perhaps *E. coli* DNAse I, or a residual DNAse activity of the RT RNAse H domain. The latter activity that has not been previously reported. Assuming that the DNase activity was occurring at the ribonuclease site of RT, we replaced Glu 478 by Gln at that site. This generated a double mutant Y188L-E478Q. Preparations of this variant did not degrade the primer.

Although HIV RT has been tested extensively for DNAse activity, the previous investigations did not use a five day incubation with single stranded substrate. Therefore, this result may indicate a hitherto undetected trace single stranded 3'-exodeoxyribonuclease activity associated with the enzyme. We cannot, however, rule out the possibility of contamination by *E. coli* DNAse I, which could be more easily separated from the double mutant than either the single mutant or native RT.

We then asked whether the variant enzyme (Y188L-E478Q) was able to PCR amplify a DNA duplex containing a py(DAD)-pu(ADA) pair. Because RT is not thermally stable, the amplification was done at 37° C., where additional RT variant was added after each heating-annealing cycle. The amplification was performed over 5 rounds, with each elongation step lasting 24 hours to allow sufficient incorporation and elongation of the NSB. An aliquot (5 µL) was removed from the reaction after each round and examined by PAGE to trace the progress of the reaction. The results (FIG. 5) display the disappearance of primer and the generation of full length product with amplification.

The PCR-amplified product was then shown to have retained the AEGIS components. To do this, a novel sequencing technique was developed to determine the amount of misincorporation at the NSB site. We found that Taq polymerase terminates the elongation of a primer when the polymerase encounters a d(puADA) in the template (FIG. 6).

Thus, the PCR generated oligonucleotide containing d(puADA), after isolation from all other PCR products and reactants, was tested for elongation termination using Taq polymerase, the natural dNTPs, and the appropriate radiolabeled primer (P1-RS). The results indicate that >95% of the primer extension stopped at position 25 (FIG. 7), establishing that the non-standard base survived the five rounds of PCR without being replaced by more than 5%.

This shows that the Y188L-E478Q variant of HIV reverse transcriptase can be used to PCR-amplify an oligonucleotide containing a single pu(ADA) or a single py(DAD). This represents the first example of an enzyme capable of replicating an artificial genetic system in this way. Further, the loss of the non standard nucleobase appears to be less than 1%, and certainly less than 2% per round.

TABLE 1

Oligonucleotides used in primer extensions and polymerase chain reactions

| | |
|---|---|
| P1-RS: | 5'-GCG AAT TAA CCC TCA CTA AAG-3' |
| P2-RS: | 5'-GCG TAA TAC GAC TCA CTA TAG-3' |
| P1-SS: | 5'-GCG AAT TAA CCC TCA CTA AAG AAC G-3' |
| P2-SS: | 5'-GCG TAA TAC GAC TCA CTA TAG ACG A-3' |
| P2-C6 | 5'-ATGCA-C6C6-GCG TAA TAC GAC TCA CTA TAG-3' (for PCR reaction) |
| P2-Rev | 5'-CGC ATT ATG CTG AGT GAT ATC-3' |
| P3: | 5'-CAG GAA ACA GCT ATG ACG-3' |
| T1: | 5'-GCGTAATACGACTCACTATAGACGTTCGTTCTTT AGTGAGGGTTAATTCGC-3' |
| T2: | 5'-GCGAATTAACCCTCACTAAAGTACGTTCGTCTA TAGTGAGTCGTATTACGC-3' |
| T1-puADA: | 5'-GCGTAATACGACTCACTATAGACGT (puADA)CGTTCTTTAGTGAGGGTTAATTCGC-3' |
| T2-pyDAD: | 5'-GCGAATTAACCCTCACTAAAGTACG (pyDAD)TCGTCTATAGTGAGTCGTATTACGC-3' |
| T3: | 5'-CGTCATAGCTGTTTCCTGGTCC(puADA)CGCATTGCTG-3' |

C6 refers to a linker that contains 3 units of polyethyleneglycol, incorporated to permit the separation of the two product strands following PCR. puADA is a nucleotide bearing the xanthine nucleobase. pyDAD is the nucleotide bearing a 2,4-diaminopyrimidine nucleobase. C6 refers to a linker that contains 3 units of polyethyleneglycol, incorporated to permit the separation of the two product strands following PCR. puADA is a nucleotide bearing the xanthine nucleobase. pyDAD is the nucleotide bearing a 2,4-diaminopyrimidine nucleobase.

REFERENCES

1. Switzer, C. Y., Moroney, S. E. and Benner, S. A. (1989) Enzymatic incorporation of a new base pair into DNA and RNA. *J. Am. Chem. Soc.,* 111, 8322-8323.
2. Piccirilli, J. A., Krauch, T., Moroney, S. E. and Benner, S. A. (1990) Extending the genetic alphabet: Enzymatic incorporation of a new base pair into DNA and RNA. *Nature,* 343, 33-37.
3. Strazewski, P. and Tamm, C. (1990) Replication experiments with nucleotide base analogs. *Angew. Chem. Int. Edit.,* 29, 36-57.
4. Rappaport, H. P. (1993) Replication of the base pair 6-thioguanine/5-methyl-2-pyrimidinone with the large Klenow fragment of *Escherichia coli* DNA-polymerase-I. *Biochemistry,* 32, 3047-3057
5. Kool, E. T. (2001) Hydrogen bonding, base stacking, and steric effects in DNA replication. *Ann. Rev. Biophys. Biomol. Struct.,* 30, 1-22.
6. Wu, Y. Q., Ogawa, A. K., Berger, M., McMinn, D. L., Schultz, P. G. and Romesberg, F. E. (2000) Efforts toward expansion of the genetic alphabet: Optimization of interbase hydrophobic interactions. *J. Am. Chem. Soc.,* 122, 7621-7632.
7. Ohtsuki, T., Kimoto, M., Ishikawa, M., Mitsui, T., Hirao, I. and Yokoyama, S. (2001) Unnatural base pairs for specific transcription. *Proc. Nat. Acad. Sci. USA,* 98, 4922-4925.
8. Goodman, M. F. (1999) On the wagon. DNA polymerase joins "H-bonds anonymous". *Nature Biotech.,* 17, 640-641
9. Service, R. (2000) Creation's Seventh Day. *Science,* 289, 232-235.
10. Watson, J. D. and Crick, F. H. C. (1953) Molecular structure of nucleic acids. A structure for deoxyribose nucleic acid. *Nature (London),* 171, 964-967.
11. Collings, et al. NAR 1997 Horn, T., Chang, C. A. and Collins, M. L. (1995) Hybridization properties of the 5-methyl-isocytidine/isoguanosine base-pair in synthetic oligodeoxynucleotides. *Tetrahedron Lett.,* 36, 2033-2036.
12. Yu, C. Z., Henry, A. A., Romesberg, F. E. and Schultz, P. G. (2002) Polymerase recognition of unnatural base pairs *Angew. Chem., Int. Ed.,* 41, 3841-3844.
13. Johnson, S. C., Sherrill, C. B., Marshall, D. J., Moser, M. J., Prudent, J. R. (2004) A third base pair for the polymerase chain reaction: inserting isoC and isoG. *Nucl. Acids Res.* 32, 1937-1941
14. Bain, J. D., Chamberlin, A. R., Switzer, C. Y. and Benner, S. A. (1992) Ribosome-mediated incorporation of non-standard amino acids into a peptide through expansion of the genetic code. *Nature,* 356, 537-539.
15. Horlacher, J., Hottiger, M., Podust, V. N., Hübscher, U. and Benner, S. A. (1995) Expanding the genetic alphabet: Recognition by viral and cellular DNA polymerases of nucleosides bearing bases with non-standard hydrogen bonding patterns. *Proc. Natl. Acad. Sci.,* 92, 6329-6333.
16. Chu, C. K., Wempen, I., Watanabe, K. A. and Fox, J. J. (1976) Nucleosides. 100. General synthesis of pyrimidine C-5 nucleosides related to pseudouridine. Synthesis of 5-(b-D-ribofuranosyl)isocytosine (pseudoisocytosine), 5-(b-D-ribofuranosyl)-2-thiouracil (2-thiopseudouridine) and 5-(b-D-ribofuranosyl)uracil (pseudouridine) *J. Org. Chem.,* 41, 2793-2797.
17. Lutz, M. J., Horlacher, J., Benner, S. A. Recognition of a non-standard base pair by thermostable DNA polymerases. *Bioorg. Med. Chem. Lett.* 8, 1149-1152 (1998)
18. Jurczyk, S. C., Horlacher, J., Devine, K. G., Benner, S. A, Battersby, T. R. Synthesis and characterization of oligonucleotides containing 2'-deoxyxanthosine using phosphoramidite chemistry. *Helv. Chim. Acta* 83, 1517-1524 (2000)
19. Van Aerschot, A., Mag, M., Herdewijn, P. and Vanderhaeghe, H. (1989) Double protection of the heterocyclic base of xanthosine and 2'-deoxyxanthosine. *Nucleos. Nucleot.,* 8, 159-178.
20. Sinha, N. D, Biernat, J. and Köster H. (1983) Beta-cyanoethyl n,n-dialkylamino/n-morpholinomonochloro phosphoamidites, new phosphitylating agents facilitating ease of deprotection and work-up of synthesized oligonucleotides. *Tetrahedron Lett.,* 24, 5843-5846.
21. Ludwig, J. and Eckstein, F (1989) Rapid and efficient synthesis of nucleoside 5'-o-(1-thiotriphosphates), 5'-triphosphates and 2',3'-cyclophosphorothioates using 2-chloro-4H-1,3,2-benzodioxaphosphorin-4-one. *J. Org. Chem.,* 54, 631-635.
22. Boyer, P. L., Tantillo, C., Jacobo-Molina, A., Nanni, R. G., Ding, J. P., Arnold, E. and Hughes, S. L. (1994) Sensitivity of wild-type human-immunodeficiency-virus type-1 reverse-transcriptase to dideoxynucleotides depends on template length—the sensitivity of drug-resistant mutants does not. *Proc. Natl Acad. Sci.,* 91, 4882-4886.

23. Bryant, F. R., Johnson, K. A. and Benkovic, S. J. (1983). Elementary steps in the DNA polymerase I reaction pathway. Biochemistry, 22, 3537-3546.
24. Kuchta, R. D. (1996). Isotopic assays of viral polymerases and related proteins. *Methods Enzymol.*, 275, 241-257.
25. Reardon, J. E. and Miller, W. H. (1990). Human immunodeficiency virus reverse transcriptase. *J. Biol. Chem.*, 265, 20302-20307.
26. Stahlhut, M. W. and Olsen, D. B. (1996). Expression and purification of retroviral HIV-1 Reverse Transcriptase. *Methods Enzymol.*, 275, 122-132.
27. Roy, K. B., and Miles, H. T. (1983) Tautomerism and ionization of xanthosine. *Nucl. Nucl.* 2, 231-242.
28. Krauch, T. *Ein neues Basenpaar Fur den genetischen Code*. Ph.D. Dissertation, ETH Nr. 8940, Swiss Federal Institute of Technology, Zurich, Switzerland, 1989.

---

What is claimed is:

1. A process for increasing the number of copies of a portion of an initial oligonucleotide, wherein said portion incorporates one or more non-standard nucleotide units incorporating the heterocycles selected from the group consisting of 2,-4-diaminoyprimidine and xanthosine, wherein said process comprises:

(a) contacting said initial oligonucleotide with an enzyme, nucleoside triphosphates that are complementary to the standard and non-standard nucleotides in the initial oligonucleotide, and a first oligonucleotide primer that is complementary to a part of said initial oligonucleotide, and incubating the contacted mixture under conditions where said enzyme synthesizes an extension product of the first primer that is complementary to said initial oligonucleotide, wherein said first primer is selected so as to be sufficiently complementary to the initial oligonucleotide that it hybridizes therewith, such that the extension product synthesized from the first primer, when it is separated from its complement, can serve as a template for synthesis;

(b) separating the extension products from the initial oligonucleotides on which they were synthesized to produce single-stranded molecules; and;

(c) adding to the mixture containing the single-stranded extension products generated from steps (a) and (b) a second oligonucleotide primer that is complementary to a part of said extension products, and incubating the mixture containing the first and second primer under conditions where the enzyme synthesizes a complement of the initial oligonucleotides as well as the extension product to generate products that are extension products of both primers, wherein said second primer is selected so as to be sufficiently complementary to the extension product of the initial oligonucleotide so that it hybridizes therewith, such that the extension product synthesized from the second primer, when it is separated from its complement, can serve as a template for synthesis.

2. The process of claim 1, wherein steps (b) and (c) are repeated at least once.

3. The process of claim 1, wherein said step (b) is accomplished by denaturing.

4. The process of claim 3, wherein said denaturing is caused by heating.

5. The process of claim 1, wherein the non standard nucleotide is retained within the product to at least 90% over 5 cycles.

6. The process of claim 1, where the enzyme is reverse transcriptase from Human Immunodeficiency Virus 1.

7. The process of claim 6, where the enzyme is a variant of reverse transcriptase from Human Immunodeficiency Virus 1 wherein site 188 holds a leucine.

8. The process of claim 6, where the enzyme is a variant of reverse transcriptase from Human Immunodeficiency Virus 1 wherein site 188 holds a leucine, and wherein site 478 holds a glutamine.

9. The process of claim 1, wherein the xanthosine is replaced by 5-aza-7-deazaxanthosine.

* * * * *